United States Patent
Blunier et al.

(10) Patent No.: US 9,572,273 B2
(45) Date of Patent: Feb. 14, 2017

(54) METHOD FOR PRODUCING A HERMETIC HOUSING FOR AN ELECTRONIC DEVICE

(71) Applicant: MB-Microtec AG, Niederwangen bei Bern (CH)

(72) Inventors: Heinz Blunier, Huenenberg See (CH); Hannes Kind, Bern (CH); Sandro M. O. L. Schneider, Thalwil (CH)

(73) Assignee: MB-Microtec AG, Niederwangen bei Bern (CH)

( * ) Notice: Subject to any disclaimer, the term of this patent is extended or adjusted under 35 U.S.C. 154(b) by 0 days.

(21) Appl. No.: 14/424,511

(22) PCT Filed: Aug. 27, 2013

(86) PCT No.: PCT/EP2013/067686
§ 371 (c)(1),
(2) Date: Feb. 27, 2015

(87) PCT Pub. No.: WO2014/033111
PCT Pub. Date: Mar. 6, 2014

(65) Prior Publication Data
US 2015/0208539 A1 Jul. 23, 2015

Related U.S. Application Data

(60) Provisional application No. 61/743,744, filed on Sep. 11, 2012, provisional application No. 61/834,514, filed on Jun. 13, 2013.

(30) Foreign Application Priority Data

Aug. 28, 2012 (AT) .................................. A 937/2012
Jun. 13, 2013 (AT) .............................. A 50386/2013

(51) Int. Cl.
*H01L 21/52* (2006.01)
*B23K 26/21* (2014.01)
(Continued)

(52) U.S. Cl.
CPC ................. *H05K 5/065* (2013.01); *A61B 1/04* (2013.01); *C03B 23/217* (2013.01);
(Continued)

(58) Field of Classification Search
CPC ...................................................... B23K 26/21
See application file for complete search history.

(56) References Cited

U.S. PATENT DOCUMENTS 2,155,449 A 4/1939 Seaman
2,953,684 A 9/1960 Machutchin et al.
(Continued)

FOREIGN PATENT DOCUMENTS

DE 1 596 843 B 7/1970
DE 2 104 763 A1 8/1972
(Continued)

OTHER PUBLICATIONS

International Search Report of PCT/EP2013/067686, mailed Mar. 17, 2014.
(Continued)

*Primary Examiner* — Stephen W Smoot
(74) *Attorney, Agent, or Firm* — Collard & Roe, P.C.

(57) ABSTRACT

A method produces a housing with at least one hermetically sealed receiving space for an electronic component, the receiving space including at least a part of the interior of the housing. In the method, a hollow body made of glass and having at least one opening is produced/provided, at least one electronic device is introduced through the at least one opening, and the receiving space is hermetically sealed by melting the housing, or the at least one opening is sealed by laser radiation. A device has an at least partially hermetically sealed housing made of silicon, particularly a housing produced according to the above-mentioned method.

39 Claims, 10 Drawing Sheets

Figure 1:
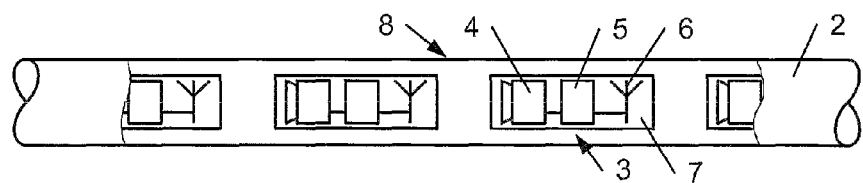

(51) Int. Cl.
  *H05K 5/06*     (2006.01)
  *H01L 23/08*    (2006.01)
  *H05K 5/00*     (2006.01)
  *A61B 1/04*     (2006.01)
  *C03B 23/217*   (2006.01)
  *C03B 23/24*    (2006.01)
  *C03B 33/08*    (2006.01)
  *C03B 33/085*   (2006.01)
  *G03B 17/08*    (2006.01)
  *H05K 5/03*     (2006.01)

(52) U.S. Cl.
  CPC .......... *C03B 23/245* (2013.01); *C03B 33/082* (2013.01); *C03B 33/0855* (2013.01); *G03B 17/08* (2013.01); *H01L 21/52* (2013.01); *H01L 23/08* (2013.01); *H05K 5/0095* (2013.01); *H05K 5/03* (2013.01)

(56) References Cited

U.S. PATENT DOCUMENTS

| | | |
|---|---|---|
| 3,026,436 A | 3/1962 | Hughes |
| 3,335,336 A | 8/1967 | Urushida et al. |
| 3,409,770 A | 11/1968 | Clapham, Jr. |
| 3,478,209 A | 11/1969 | Feuer |
| 3,566,125 A | 2/1971 | Linhart, Jr. et al. |
| 3,908,266 A | 9/1975 | Hill et al. |
| 3,920,996 A | 11/1975 | Moore, III |
| 4,126,384 A | 11/1978 | Goodman et al. |
| 4,214,820 A | 7/1980 | Leibowitz et al. |
| 4,414,460 A | 11/1983 | Sudo et al. |
| 4,869,744 A * | 9/1989 | Romberg .............. C03B 23/092 65/105 |
| 4,990,804 A | 2/1991 | McNair |
| 5,025,550 A | 6/1991 | Zirbes et al. |
| 6,176,753 B1 | 1/2001 | Pong et al. |
| 2002/0125816 A1 | 9/2002 | Dunham et al. |
| 2004/0237422 A1* | 12/2004 | Tat ...................... B29C 65/1435 52/79.1 |
| 2006/0174658 A1 | 8/2006 | Huang et al. |
| 2007/0001579 A1 | 1/2007 | Jeon et al. |

FOREIGN PATENT DOCUMENTS

| | | |
|---|---|---|
| DE | 2 237 616 A1 | 3/1974 |
| DE | 25 38 806 A1 | 7/1976 |
| DE | 10 2006 024 566 A1 | 8/2007 |
| EP | 0 055 416 A2 | 7/1982 |
| EP | 0 062 604 A1 | 10/1982 |
| EP | 0 069 311 A1 | 1/1983 |
| EP | 1 216 971 A1 | 6/2002 |
| EP | 1 741 510 A1 | 1/2007 |
| JP | S51-81638 A | 7/1976 |
| JP | S54 19573 A | 2/1979 |
| JP | S54 19574 A | 2/1979 |
| JP | 2005-066629 A | 3/2005 |
| JP | 2009/015131 A | 1/2009 |
| KR | 2008-0023485 A | 3/2008 |
| WO | 2008/035770 A1 | 3/2008 |

OTHER PUBLICATIONS

International Search Report of PCT/EP2013/067776, mailed Feb. 28, 2014.

* cited by examiner

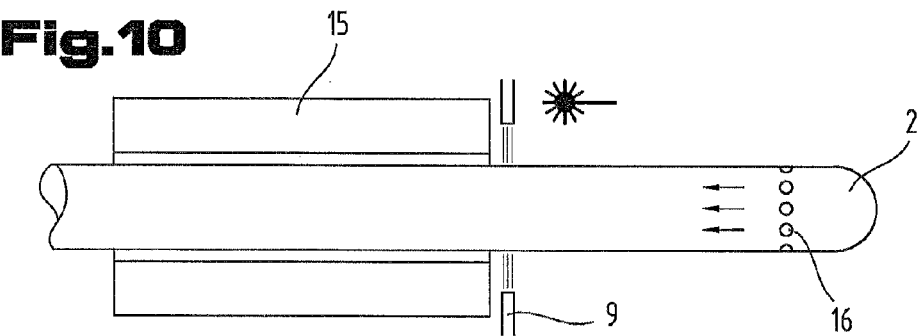
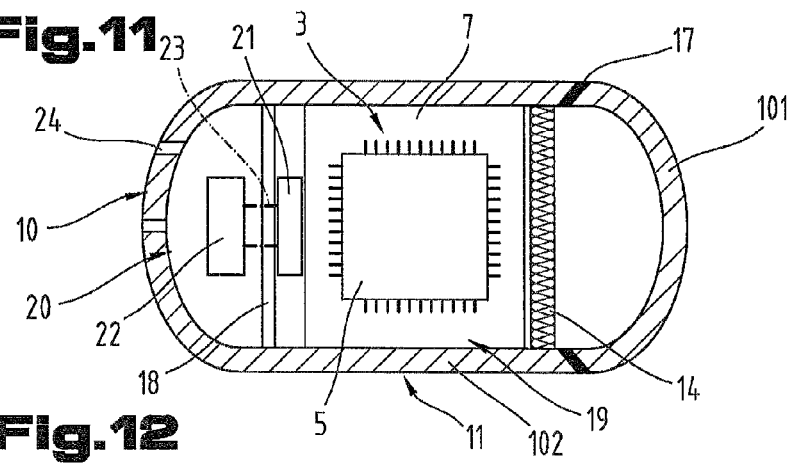
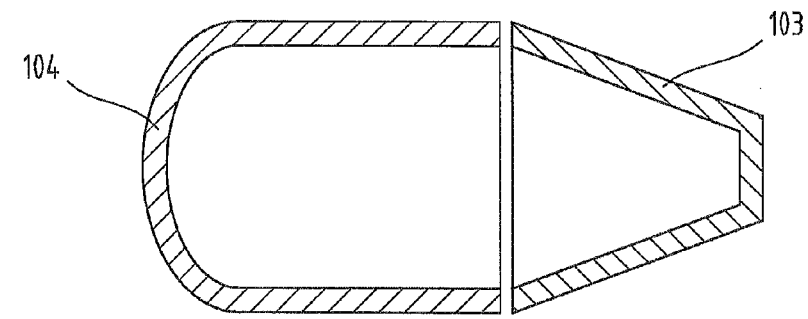
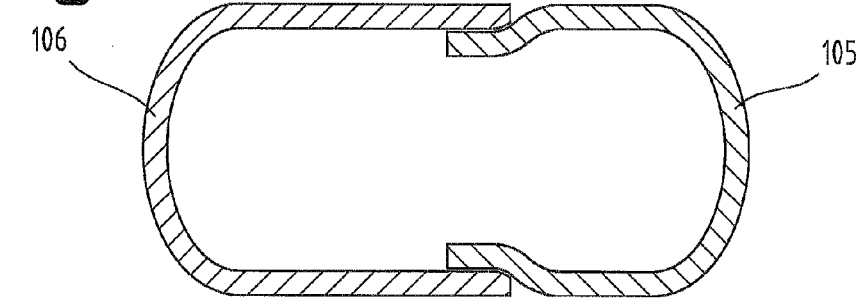

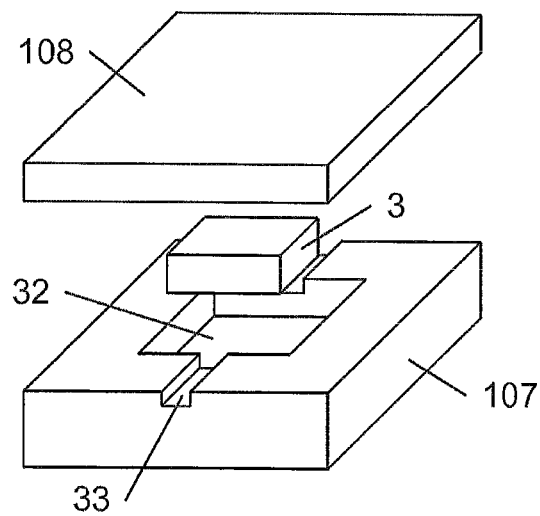
Fig. 17
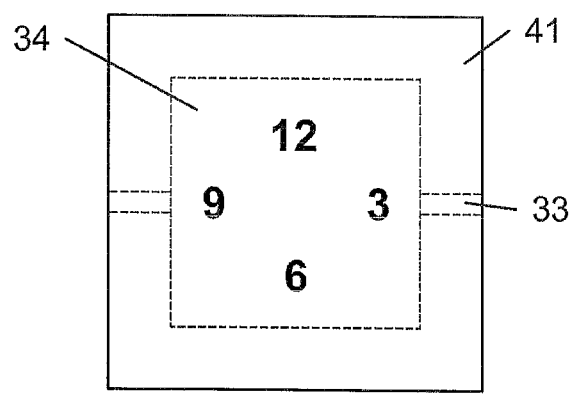
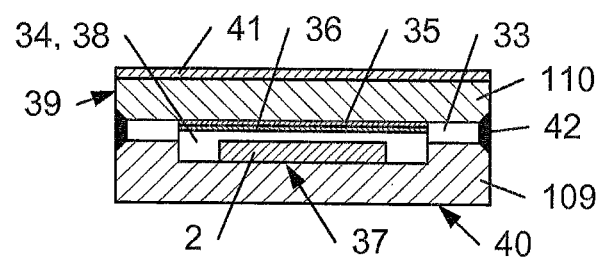
Fig. 18

METHOD FOR PRODUCING A HERMETIC HOUSING FOR AN ELECTRONIC DEVICE

CROSS REFERENCE TO RELATED APPLICATIONS

This application is the National Stage of PCT/EP2013/067686 filed on Aug. 27, 2013, which claims priority under 35 U.S.C. §119(e) of U.S. Provisional Application Ser. No. 61/743,744 filed on Sep. 11, 2012, and 61/834,514 filed on Jun. 13, 2013, and under 35 U.S.C. §119 of Austrian Application Nos. A 937/2012 filed on Aug. 28, 2012, and A 50386/2013 filed on Jun. 13, 2013, the disclosures of which are incorporated by reference. The international application under PCT article 21(2) was not published in English.

The invention relates to a method for the production of a hermetic housing for an electronic device, as well as to an apparatus having a housing that is hermetically sealed, at least in part.

Hermetic housings for electronic devices are fundamentally known. They protect the electronic devices from external influences and are liquid-tight and/or gas-tight. Vice versa, however, protection of the surroundings can also be a criterion that must be taken into consideration when using hermetic housings, if the electronic device represents a hazard for these surroundings. Examples that can be listed are medical implants (e.g. cardiac pacemakers, insulin pumps, and the like), in which the electronic device must be protected from contact with bodily fluids, but, on the other hand, the organism must also be protected from uncontrolled emission of hazardous substances by the device. In particular, in such an application, attention must also be paid to ensure that the housing itself does not emit any hazardous substances. Conventional production methods for such arrangements are therefore comparatively complicated.

For the production of such hermetically sealed housings, particularly made of transparent materials such as glass, for example, it is already known to use laser radiation, for example also ultra-short pulses of such laser beams, to close off these housings. Such methods and apparatuses are known from JP 2005/66629 A as well as WO 2008/035770 or also EP 1 741 510 A1, for example. It is a disadvantage of these methods and apparatuses that they can only be used for connecting flat, planar components.

It is therefore a task of the invention to indicate an improved method for the production of a hermetic housing for an electronic device.

The task of the invention is accomplished by a method for the production of a housing having at least one hermetically sealed accommodation space for an electronic device, comprising at least a part of an interior of the housing, comprising the steps:
producing/making available a hollow body made of glass, having at least one opening,
introducing, positioning and/or fixing in place at least one electronic device through the at least one opening,
hermetically sealing the accommodation space by means of melting the housing, or
closing off and welding the at least one opening by means of laser radiation.

In this way, a hermetic housing for an electronic device can be produced in simple manner. The housing can consist entirely of the same material, namely glass, by means of melting the opening(s). As a result, good protection of the electronic device, on the one hand, but also of the surroundings in which the device is operated, on the other hand, is guaranteed. Glass is resistant to most chemical substances and itself does not emit any substances, in other words it is inert. In particular, the aforementioned properties apply for boron silicate glass or other types of glass that have the same properties.

Further advantageous embodiments of the production method are evident from the following description, particularly in connection with the figures.

It is advantageous if a heat insulator or a heat protection layer is disposed between the device and the melting region or welding region, or if a heat insulation apparatus is disposed between the electronic device and at least one of the two face walls. In this way, the electronic device can be effectively protected from the heat that occurs during the severing process or welding process.

It is advantageous if multiple electronic devices are introduced, positioned and/or fixed in place in a tubular housing, at a distance from one another in the longitudinal direction, one after the other, through the at least one opening, whereupon the housing is heated by means of laser radiation, by emission of nanosecond and/or picosecond energy pulses or with continuous introduction of energy in the intermediate region between the electronic devices, and the tubular housing is closed off with a face wall, by means of differently great forces exerted on the inside and outside of the housing in the region of the severing location, in the longitudinal direction of the housing, on both sides of the intermediate region. In particular, differently great forces can be exerted on the inside and outside of the housing in the region of the severing location, in the longitudinal direction of the housing, during the severing process and/or closing process of the tubular housing. Specifically, the inside and outside of the housing can have a differently great pressure force exerted on them in the region of the severing location, during the severing process and/or closing process of the tubular housing. In this manner, the housings can be produced particularly efficiently. In particular, the housing can be flexibly structured by means of the differently great forces.

In this connection, it is also advantageous if a face wall of the housing is heated by heating the end region of the center part by means of a laser, by emission of nanosecond and/or picosecond energy pulses, and a face wall is formed by the differently great forces exerted on the inside and outside of the housing in the region of the severing location, in the longitudinal direction of the housing. As a result, the face wall can be formed without a special component being required for this purpose.

It is also advantageous if a partition wall is inserted into the interior and welded to the housing, and the two accommodation spaces are hermetically separated from one another. In particular, it is advantageous, in this connection, if an electronic device and/or an energy source is/are disposed in a first hermetically sealed accommodation space. It is furthermore particularly advantageous, in this connection, if at least one of the elements mentioned below, such as an electronic device, analysis apparatus, readings recorder is disposed in an accommodation space adjacent to the first hermetically sealed accommodation space. In this way, it is possible to dispose different components of the electronic device in different accommodation spaces. For example, a gas sensor can be disposed in one accommodation space, and evaluation electronics can be disposed in another accommodation space, in order to protect the evaluation electronics, for example, from reactive gases that reach the gas sensor.

It is particularly advantageous if the housing has at least one opening that extends from the outside at least into one of the two partial spaces, which opening is air-permeable and/or liquid-permeable. In this manner, a connection from the analysis apparatus or the readings recorder to the surroundings of the housing can be provided. For example, a gas sensor can examine the air surrounding the housing in this manner. Of course, the measurement is not restricted to gases, and instead, liquids can also be examined. For example, the sensor can be configured as a pH sensor for liquids.

It is advantageous, in this connection, if the analysis and evaluation unit is configured for analysis and evaluation of bodily fluids and/or tissue samples. Specifically because of the small dimensions of the housing, it can be used well in the human or animal body.

It is particularly advantageous if openings are disposed in the partition wall between the first hermetic accommodation space and the second hermetic accommodation space, which openings can be hermetically sealed by means of light guides, electric lines or conductive contact masses. In this way, data and/or energy can be exchanged between the two accommodation spaces, for example. Electric, optical, pneumatic or hydraulic lines can be provided, for example.

It is advantageous if the dew point of the water vapor in the air in the housing, at least in its hermetically sealed partial space, amounts to 0°, preferably to between −10° C. and −30° C. In this way, condensation on the inside walls of the housing at its operating temperature can be prevented.

It is furthermore advantageous if the partial space is configured to be water-vapor-tight with a water vapor permeability $s_d$ greater than 2,500 m. In this manner, diffusion of water vapor into the housing and, as a consequence, an undesirable increase in the humidity within the same, can be prevented.

It is advantageous if a camera is introduced into the cavity, or if an image recording device, for example an image recognition chip, is disposed in the housing. In this manner, the apparatus that is formed can be used for observation, wherein the transparent housing proves to be a particularly advantage.

It is also advantageous if a wireless module and/or a transponder is/are introduced into the cavity. In this way, it is possible for data to be read out from the electronic device or transmitted to it.

It is particularly advantageous if a mass moved by a motor is introduced into the cavity. In this way, it is possible to move the housing with the electronic device from one location to another. For this purpose, the said mass can be moved translationally and/or rotationally. As a result of the counter-force that occurs, or of the counter-torque that occurs, the housing with the electronic device is put into motion. It is particularly advantageous, in the case of this drive, that the housing does not have to have any kind of openings toward the outside.

It is also advantageous if a repulsion drive having a passage opening in the housing is introduced into the cavity. This is a further possibility for putting the housing with the electronic device into motion. Pumps, compressors, but also containers that are under pressure, the content of which is discharged in controlled manner, can be used for this purpose, for example. It is advantageous that a constant drive force can be implemented with such a repulsion drive.

It is particularly advantageous if a tritium gas light source is disposed in the cavity. In particular, if a camera is also disposed in the cavity, a particularly advantageous arrangement is obtained in this manner, because the tritium gas light source can illumine the viewing field of the camera, without external energy being required for this purpose. Alternatively or in addition, an LED or a luminescent material with afterglow properties can also be disposed in the housing.

In this connection, it is advantageous if the partial space is configured to be gas-tight, particularly tritium-gas-tight. In this way, escape of a gas, particularly of the tritium gas that emits a decay radiation, into another partial space or into the surroundings of the housing can be prevented.

It is furthermore advantageous if at least one of the components in the housing listed below, such as light source, image recognition apparatus, image recording apparatus, electronic device, analysis, memory and evaluation unit, is connected with a transmitter for wireless transmission of data. In this manner, data determined can be passed on to external evaluation units.

It is also advantageous if at least one of the components in the housing listed below, such as light source, image recognition apparatus, image recording apparatus, electronic device, analysis and evaluation unit is connected with an energy source. In this way, the modules disposed in the housing can be operated without an external energy supply.

It is particularly advantageous if the energy source is connected with an energy converter to which energy can be applied in contact-free manner. In this manner, energy can be transmitted to the interior of the housing without having to perforate the housing wall for this purpose. For example, the energy can be transmitted inductively, e.g. by infrared or ultrasound. It is also conceivable that the energy converter converts movement energy of the housing to electric energy, as is known for automatic watches, for example.

It is advantageous if at least one end of a tubular base body is melted/welded for production of the housing. In this way, it is possible to close off one end or both ends of the tube, without using additional materials.

It is particularly advantageous if a tubular base body is severed by means of melting it, for production of the housing, wherein the melted material closes off the resulting ends. In this way, production of the housing is possible in particularly efficient manner, because the tubular base body, and, at the same time, one end of two housings, in each instance, are formed in one work step. The tube itself can have not only a circular cross-section but also a polygon-shaped, particularly square, as well as an oval cross-section.

In this connection, it is particularly advantageous if the tubular base body is subjected to tensile stress during the severing process. In this way, the severing process and also closing of the resulting tube ends are promoted.

It is advantageous if an opening in the housing is melted/welded using a laser. In this way, it is possible to close off the opening without the use of additional materials.

It is advantageous if at least one of the face walls is configured to be convex. In particular, it is advantageous if the face walls are configured with a cone that extends in the direction facing away from the center part or as a spherical dome or spherical dome section. In this way, great pressure stability and resistance to implosion and explosion is achieved. However, it is also advantageous if alternatively, at least one of the face walls is configured to be concave or planar.

It is also advantageous if the housing is formed from a cylindrical center part and two face walls that are disposed in the face sides of the same. In this way, the housing can be produced from a tubular base body.

It is advantageous if a wall thickness of the housing, at least in the center range, amounts to 0.05 to 5 mm. In this way, sufficient stability to withstand the most frequent stresses that occur during operation can be achieved.

It is advantageous if micro-bores are disposed in the housing, which are gas-permeable but liquid-impermeable. In this way, the electronic device can be cooled, particularly even if it is operated in a liquid.

It is particularly advantageous if the housing, with the electronic device, is introduced into a further hermetic glass housing, in which micro-bores are disposed, which are gas-permeable but liquid-impermeable. In this way, the electronic device can be cooled without being exposed to the gas that passes through the micro-bores. This is particularly advantageous in the case of sensitive electronic devices and/or aggressive gases.

It is advantageous if bores for passing through metallic wires and/or light-guide fibers are disposed in the housing. In this manner, electric energy or radiation energy and/or data can be transmitted through the housing.

It is advantageous if the outer surface of the housing is coated with a gel and/or a flavor carrier. The electronic device encapsulated in the glass housing can be intended for use in the human or animal body, particularly for being swallowed by humans or animals. In order to promote or facilitate this swallowing, the surface of the housing can be coated with a gel and/or flavor carrier, as mentioned.

It is also advantageous if the outer surface of the housing is roughened and/or provided with reactive substances/structures that promote growth of human/animal/plant tissue on it. This variant is particularly advantageous if the electronic device encapsulated in the glass housing is supposed to be anchored in place in the tissue, particularly by means of an invasive operation.

It is advantageous if the housing consists of two housing parts and the two housing parts are welded to one another by means of laser radiation with emission of energy in the nanosecond and/or picosecond range, pulsed or continuous. In this way, the energy required for welding can be metered well and the electronic device can thereby be effectively protected against the action of heat. It is advantageous, in this connection, if the emission of energy of the laser pulses is controlled with a control apparatus, in such a manner that the temperature in the interior of the housing is kept below a value of 200° in a region that is at a distance of equal to or greater than 2 mm from the weld seam or from the location of action of the laser beams. In this case, it can be assumed, with very great likelihood, that the electronic device will not be damaged by the effect of the laser radiation.

It is particularly advantageous if the regions adjacent to the weld seam are cooled during application of the heat energy by means of the laser radiation. In this way, the electronic device can be protected even better from the heat that results from the laser radiation.

It is advantageous if the method for the production of a hermetic housing for an electronic device comprises the following steps:
  making at least one depression in at least one housing part of a housing,
  producing at least one cavity by means of joining the housing parts together, wherein at least one opening, particularly at least two openings, remains/remain open into the cavity from the outside,
  introducing an electronic device into the at least one cavity through the at least one opening, and
  closing off and welding the at least one opening by means of laser radiation.

In this way, block-shaped or planar housings, in particular, can be formed for electronic devices. In this connection, it is particularly advantageous if the one housing part is formed by a plate-shaped cover layer.

It is advantageous if the aforementioned method additionally comprises the following steps:
  producing a fluorescent and/or phosphorescent layer formed from a substance that can be excited to produce light, by means of decay radiation, on at least part of a delimitation wall of the at least one cavity, and
  introducing a medium that emits a decay radiation for a substance that can be excited to produce light into the at least one cavity, through the at least one opening.

In this way, the housing can be equipped with self-luminous surfaces. By means of selective coating of at least one housing part with a fluorescent and/or phosphorescent substance, the light-emitting surface can furthermore be structured well. In this way, any desired luminous letters, numbers, symbols or other geometric surfaces can be implemented, among other things.

Also advantageous is a method for the production of self-luminous bodies, comprising the steps:
  making at least one depression in at least one housing part of a housing,
  producing a fluorescent and/or phosphorescent layer formed from a substance that can be excited to produce light, by means of decay radiation, and/or a mask on at least part of a delimitation wall of at least one cavity,
  producing the at least one cavity by means of joining the housing parts together,
  welding the housing parts by means of laser radiation, by emission of nanosecond and/or picosecond energy pulses and/or continuously, wherein at least one feeder opening, particularly at least two feeder openings, remains/remain open into the cavity from the outside,
  introducing a medium that emits a decay radiation for a substance that can be excited to produce light, or the substance and the medium, into the at least one cavity, through the at least one feeder opening, and
  closing off and welding the at least one feeder opening by means of heat effect by means of laser radiation and/or a gas flame.

It is advantageous, in this connection, if the laser radiation is formed by means of nanosecond and/or picosecond energy pulses and/or continuously, because the laser power supplied can be well influenced in this manner.

It is advantageous if at least a part of the housing or of the cover layer is produced in diffuse manner. As a result, the planar light emission can be even further improved.

It is also advantageous, however, if at least a part of the housing or of the cover layer is configured to be opaque. In this way, the penetration of light through regions of the housing or also through the entire housing can be prevented. In particular, these opaque regions are suitable for forming a mask.

It is advantageous if the diffuse or opaque parts of the housing or of the cover layer are disposed adjacent to the melting regions or welding regions. In this way, it is possible to connect diffuse and opaque housing parts with one another and to thereby create different partial regions of the housing.

It is also advantageous if at least a part of the housing or of the cover layer is provided with a functional coating, for example a film. In particular, the functional coating, for example the film, can be configured to be diffuse or opaque. In this way, it is possible, for example, to structure a housing having essentially homogeneous optical properties to be optically different. For this purpose, the housing is simply coated and/or adhesively covered with a film. Of course, the functional coating and/or film is/are not restricted to optical properties, but rather can also influence other physical properties, for example electrical conductivity.

It is advantageous if the housing that is composed of silicon and hermetically sealed, at least in part, is produced in one piece from a single basic material. Because the housing is in one piece, its tightness can be guaranteed particularly well.

It is furthermore advantageous if the housing that is composed of silicon and hermetically sealed, at least in part, consists of multiple housing parts and is produced at least from a single basic material. As a result, production of the housing can take place in simple manner, because joining of the parts is generally non-problematical, because only one material is used.

It is also advantageous if the housing parts are formed from different materials, which have essentially the same physical and chemical properties. As a result, production of the housing can also take place in simple manner, because joining of the parts composed of materials having similar properties is generally non-problematical.

It is advantageous if the fluorescent and/or phosphorescent layer is produced by means of coating the housing part and/or the housing parts with an adhesive and subsequently applying a fluorescent and/or phosphorescent substance onto the adhesive layer. In this way, even fluorescent and/or phosphorescent media that have no or few adhesion properties or adhesive properties can be used for the coating. Coating of the housing part with the fluorescent and/or phosphorescent substance (e.g. ZnS and/or ZnO) can take place by means of stamping, for example, as well as by means of sputtering.

It is particularly advantageous if the adhesive and/or the fluorescent and/or phosphorescent substance or the fluorescent and/or phosphorescent layer is/are applied to the housing part and/or the housing parts before production of the cavity. In this way, the housing part and/or the housing parts can be selectively coated with adhesive and/or a fluorescent and/or phosphorescent substance, in comparatively simple manner. For example, the layers can be sprayed on or rolled on, particularly using masks. It is also conceivable, for example, to imprint the layers or to stamp them on.

It is also advantageous if the adhesive and/or the fluorescent and/or phosphorescent substance or the fluorescent and/or phosphorescent layer is/are introduced into the (finished) cavity through the at least one feeder opening. In this way, luminous layers having a large area (and particularly layers that are unstructured) can be produced in simple manner.

It is particularly advantageous if the adhesive is applied to the housing part and/or the housing parts before the cavity is produced, and the fluorescent and/or phosphorescent substance is introduced into the cavity through the at least one feeder opening. In the case of this variant, selective wetting of the housing part and/or of the housing parts with adhesive is therefore combined with simple deposition of the fluorescent and/or phosphorescent substance. In this way, a simple method for the production of structured luminous surfaces is obtained.

In general, the fluorescent and/or phosphorescent substance can be introduced as a powder, as a gel, in the gas phase or as a solution. In particular, in this connection the flow behavior of the stated substance can be improved by means of providing a micro-structure or nano-structure.

Advantageous possibilities for applying the fluorescent and/or phosphorescent substance to the housing parts are sputtering, vapor-depositing, spraying, rolling or spin-coating it on.

It is advantageous if the depression is mechanically produced in the housing part (e.g. by means of milling, ultrasound drilling) or using ion-beam removal, laser-beam removal, powder blasting or chemical etching. All these methods allow production of a depression within the scope of a proven production process, which thereby takes place in controlled manner.

It is advantageous if a mask is disposed between the housing parts or on them. In particular, the mask can also be disposed between the fluorescent and/or phosphorescent layer and at least one housing part. In this way, it is possible to produce luminous letters, numbers, symbols, and geometrical surfaces, for example, without the fluorescent and/or phosphorescent layer having to be structured for this purpose. Instead, an unstructured fluorescent and/or phosphorescent layer is combined with a structured mask, which allows the light produced to partially pass through, or partially reflects or absorbs it.

It is advantageous if the housing parts as well as, if applicable, the mask are connected with one another by means of fusion bonding, for example at temperatures of 700-800° C. In this connection, the boundary surfaces of the connected parts are held together by means of van der Waals' forces.

It is also advantageous if the housing parts and, if applicable, the mask are connected with one another by means of anodic bonding, for example at temperatures of 350-450° C. In this method, a chemical bond is initiated at the boundary surfaces of the parts to be connected, by means of electrical attraction forces, in other words by applying an electrical voltage.

It is advantageous if the at least one feeder opening is welded shut using a laser. In this way, it is possible to close the feeder opening without the aid of additional substances. At this point, it is noted that methods for welding glass parts, using a laser, are known as such, for example from EP 1 741 510 A1.

It is advantageous if
 glass or silicon is provided for a housing part and/or
 glass or boron silicate is provided for a housing part and/or
 zinc sulfide (ZnS) is introduced as a fluorescent and/or phosphorescent substance, and/or
 phosphoric acid ($H_3PO_4$) is applied as an adhesive and/or
 tritium gas is introduced as a medium that emits decay radiation.

Particularly by means of the use of zinc sulfide (ZnS) and tritium gas, the self-luminous body is implemented using means that are proven in connection with tritium gas lights, so that great reliability of the self-luminous body being presented can also be assumed.

In this connection, it is advantageous if phosphoric acid ($H_3PO_4$) is applied as an adhesive, and if zinc sulfide (ZnS) is introduced as a fluorescent and/or phosphorescent substance. It has an advantageous effect, in this connection, that phosphoric acid as such does not have any excessive adhesion properties, and only forms an adhesive layer in combination with zinc sulfide (ZnS). The adhesive, which is present in the form of phosphoric acid, can thereby be applied in very differentiated manner, thereby making it possible to produce fine structures. For example, the phosphoric acid can be applied using the ink-jet printing method.

However, it is also advantageous if a mixture of phosphoric acid ($H_3PO_4$) and zinc sulfide (ZnS) is applied as the fluorescent and/or phosphorescent layer. In the case of this variant, a substance that is adhesive in and of itself is therefore applied to a housing part. This variant is therefore particularly suitable for imprinting (for example using the calender printing method or stamping method).

It is advantageous if at least one of the housing parts is provided with support elements disposed distributed over the surface area of the cavity, which elements extend in the direction of the other housing part, and if the housing parts are supported on one another by way of these support elements. In this manner, the housing parts are prevented from being excessively bent relative to one another.

In this connection, it is furthermore advantageous if at least one of the two housing parts is connected with the support elements. In this way, the support elements can be positioned well in the cavity. If the support elements are connected with both housing parts, tensile forces and shear forces can also be better transferred between them.

It is advantageous if the housing is configured as a block or flat piece, particularly if the block or flat piece is formed by two essentially plate-shaped housing parts having a polygonal or elliptical or circular base surface, and if the sum of the heights of the two housing parts that are perpendicular to the base surface is less than the shorter side length or a minimal diameter or radius of the same. In this manner, the light-emitting surface area is relatively large in proportion to the volume of the self-luminous body.

Supplementally, it is noted that the embodiment variants disclosed with regard to the method and the resulting advantages apply in the same manner to the variants and advantages presented with regard to the self-luminous body, and vice versa.

For a better understanding of the invention, it will now be explained in greater detail using the following figures.

Figure 2:
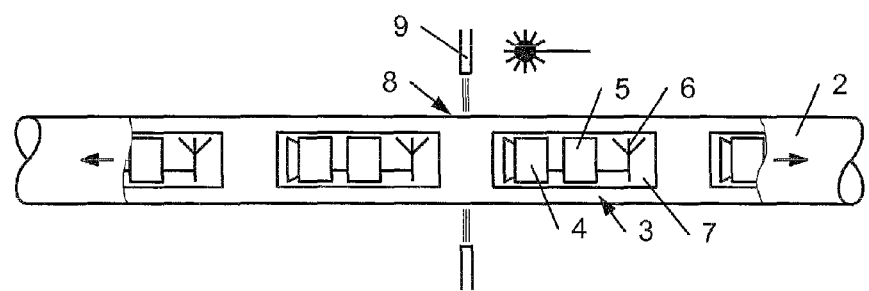
Figure 3:
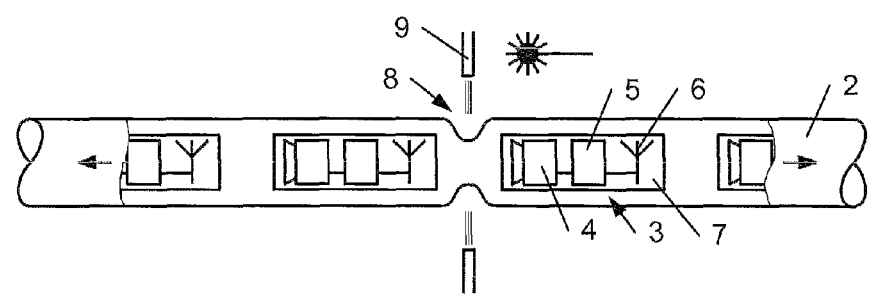
Figure 4:
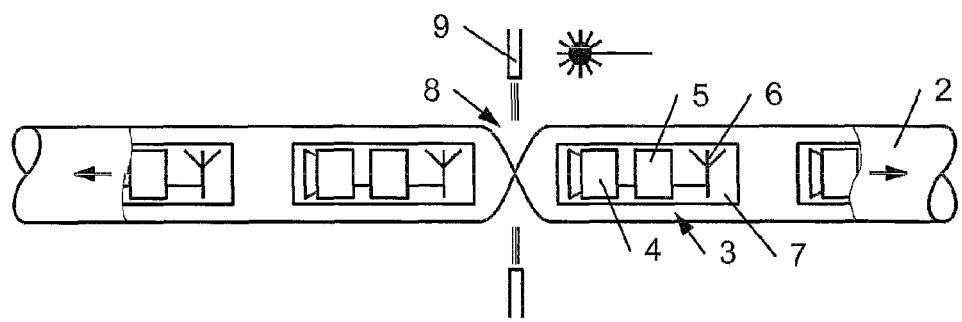
Figure 5:
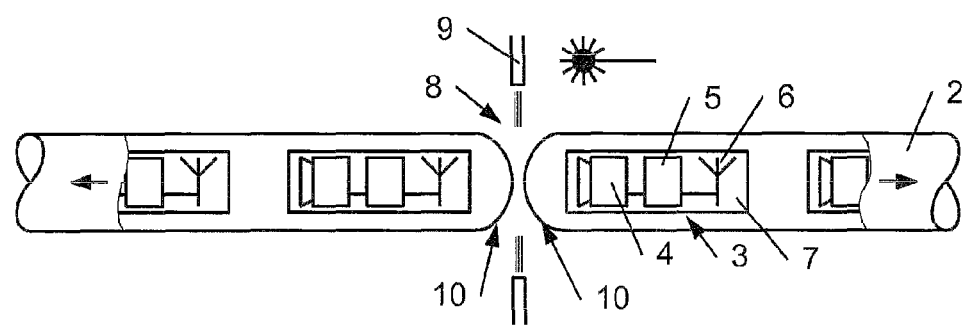
Figure 6:
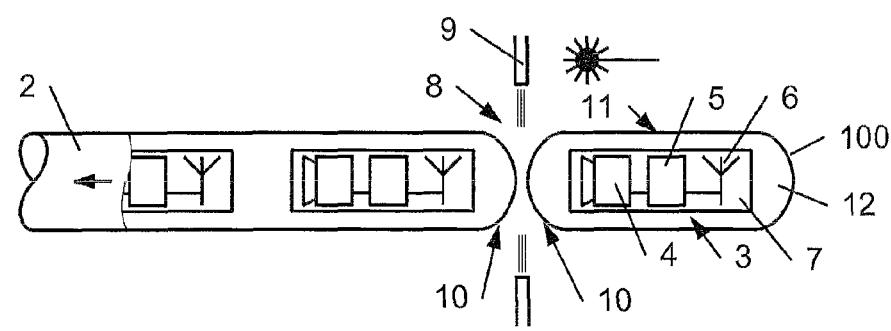
Figure 7:
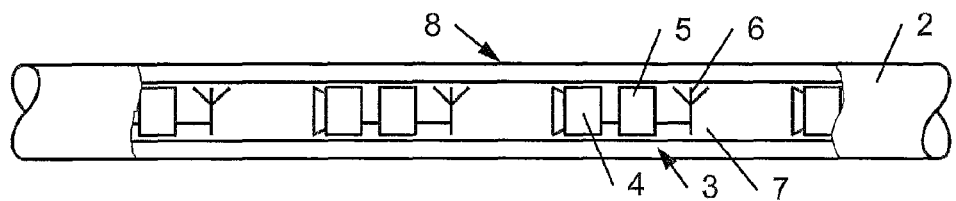
Figure 8:
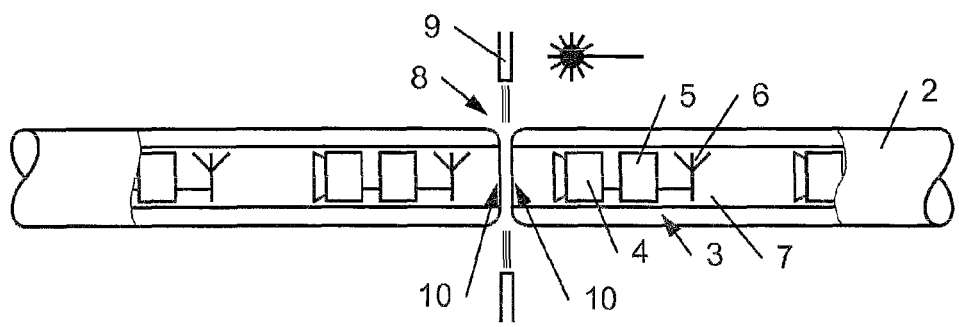
Figure 9:
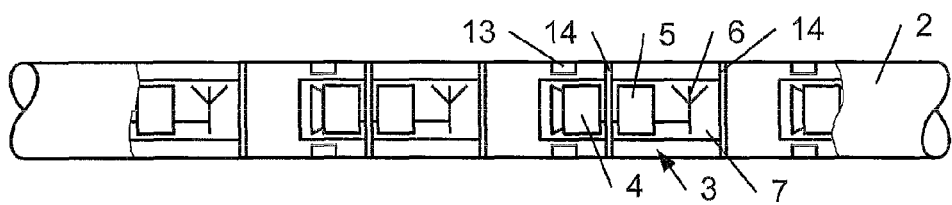
Figure 14:
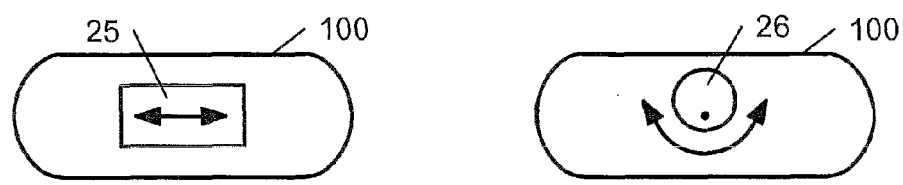
Figure 15:
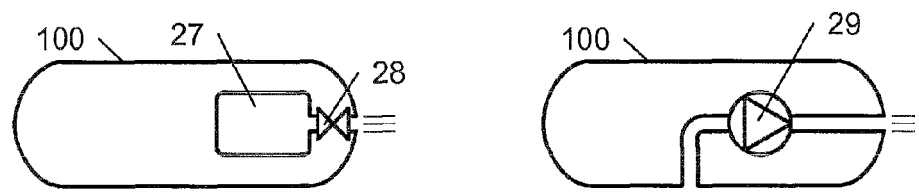
Figure 16:
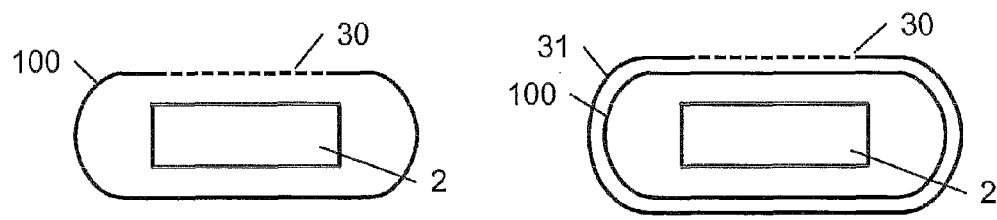
Figure 19:
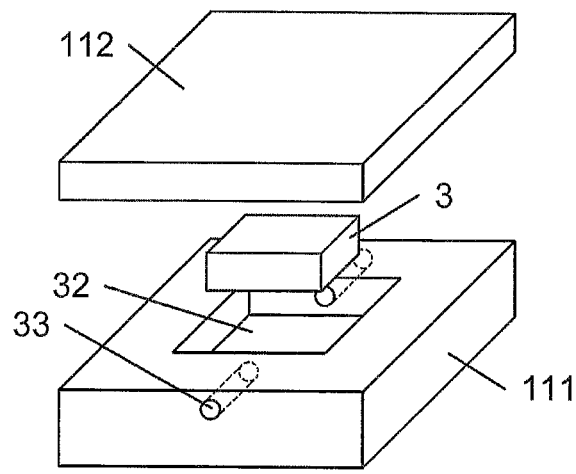
Figure 20:
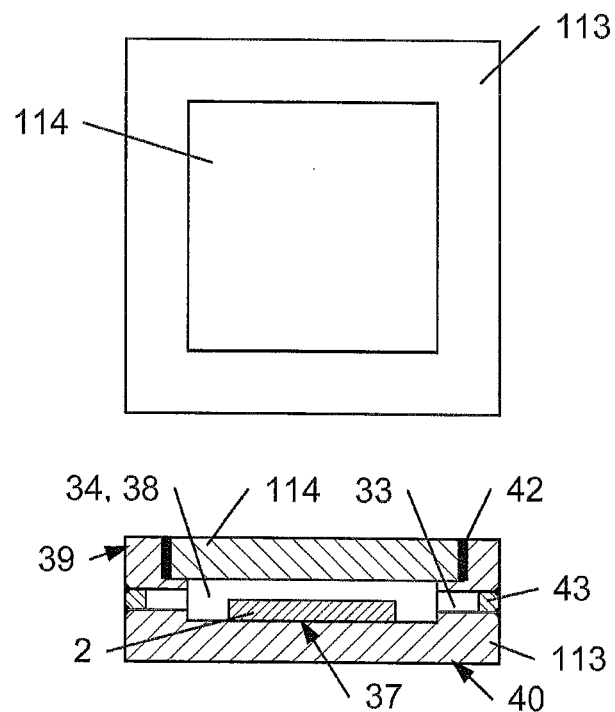
Figure 21:
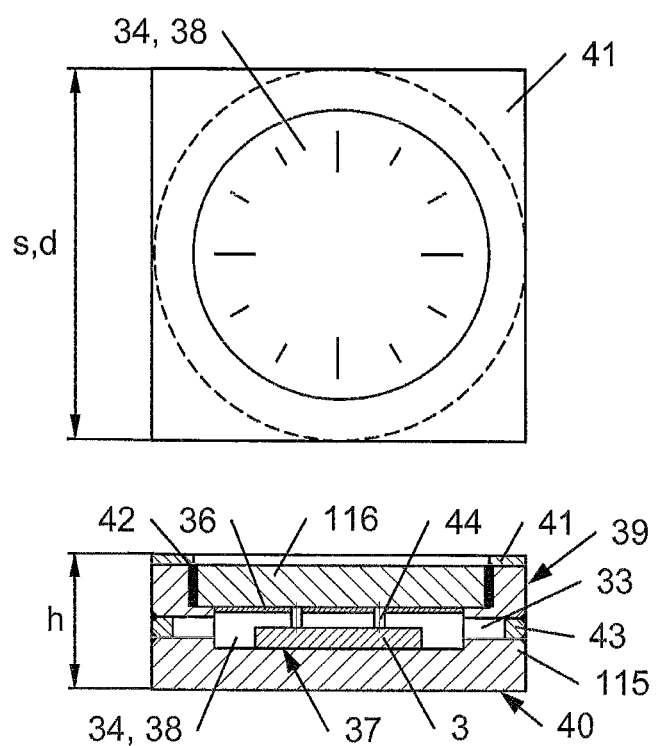
Figure 22:
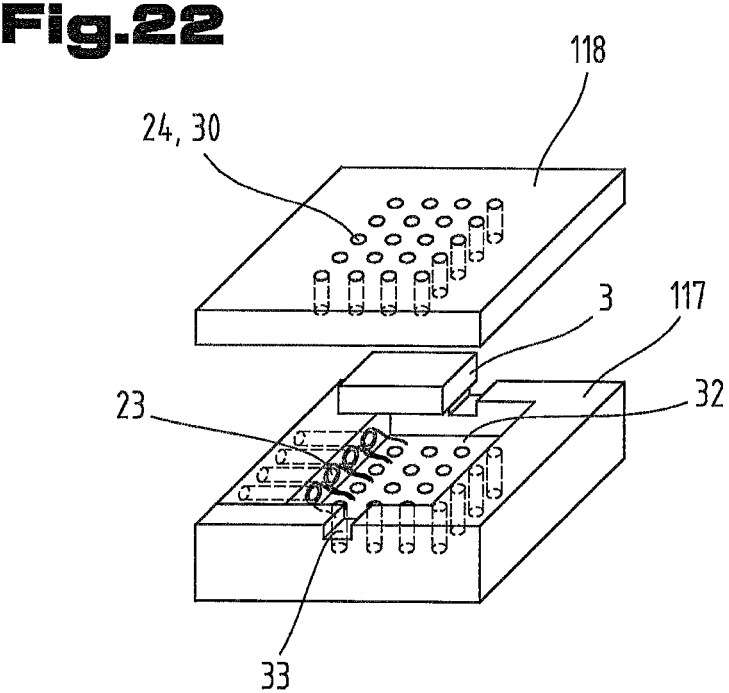
Figure 23:
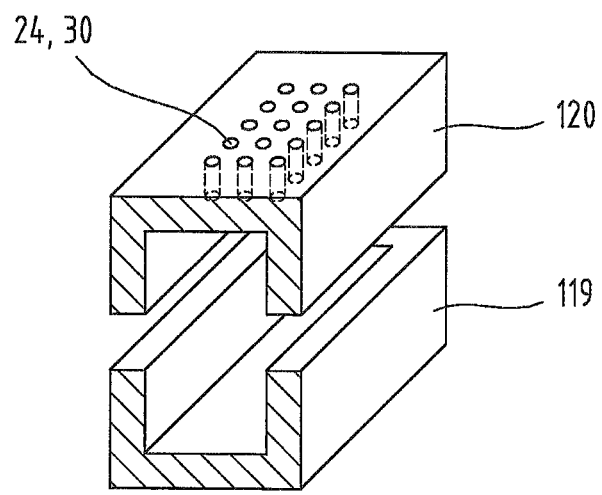
Figure 24:
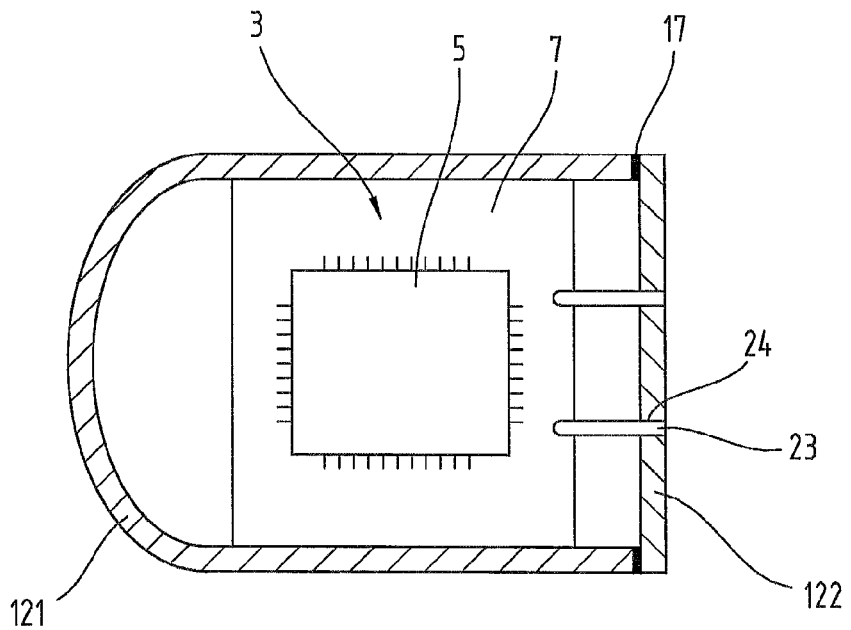
Figure 25:
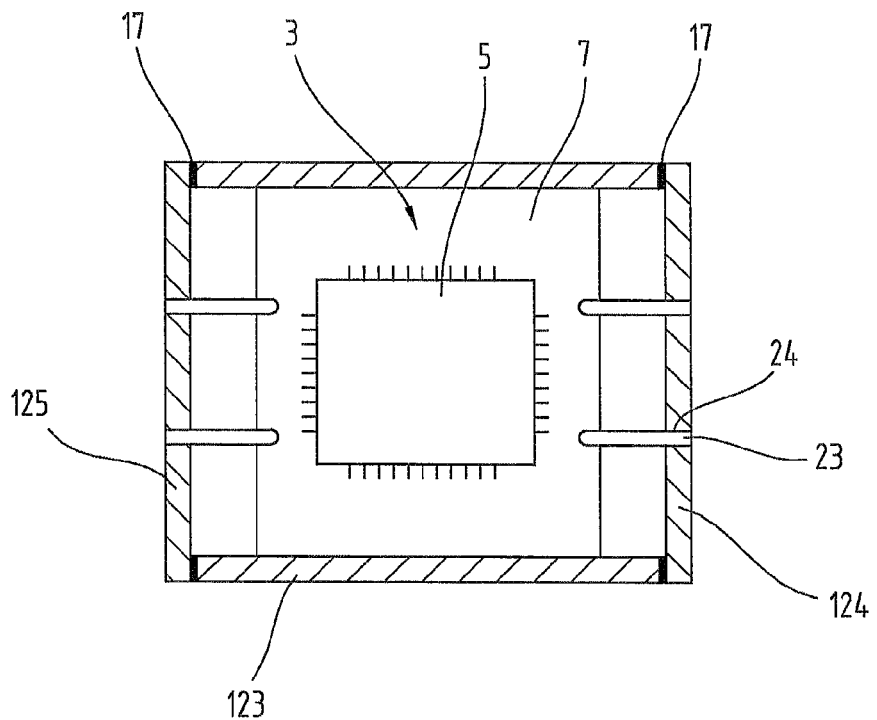

These show, each in a greatly schematic simplified representation:

FIG. 1 a tubular base body having multiple electronic devices disposed within it;

FIG. 2 the arrangement from FIG. 1, which is irradiated by a laser in a region between two electronic devices;

FIG. 3 the arrangement from FIG. 2 with a starting constriction in the severing region;

FIG. 4 the arrangement from FIG. 2 with an advanced constriction in the severing region;

FIG. 5 the arrangement from FIG. 2 with a completely severed base body;

FIG. 6 the arrangement from FIG. 5 with a completed housing;

FIG. 7 like FIG. 1, only with a continuous circuit board;

FIG. 8 like FIG. 7, only with a severed tubular body and severed circuit board;

FIG. 9 like FIG. 1, only with tritium gas light sources and thermal partition walls;

FIG. 10 a cooling possibility for the tubular body;

FIG. 11 an exemplary electronic device in detail;

FIG. 12 a housing having a conical face wall;

FIG. 13 a housing having an overlapping connection region;

FIG. 14 drive possibilities for the electronic device, using moved masses;

FIG. 15 drive possibilities for the electronic device, according to the repulsion principle;

FIG. 16 housing having micro-bores;

FIG. 17 a block-shaped housing for an electronic device, in an exploded representation;

FIG. 18 an exemplary electronic device having a housing in the form of a watch face;

FIG. 19 like FIG. 17, only with a feeder opening configured in a different manner;

FIG. 20 a variant of a planar housing for an electronic device;

FIG. 21 a further exemplary electronic device having a housing in the form of a watch face;

FIG. 22 a planar, two-part housing with micro-bores or passage bores;

FIG. 23 a housing that consists of two parts shaped essentially as a U profile;

FIG. 24 a housing that comprises a housing part similar to a test tube and a plate-shaped housing part connected with it; and FIG. 25 a housing that comprises a tubular housing part that is closed off, on both sides, with plate-shaped housing parts.

As an introduction, it should be stated that in the different embodiments that are described, the same parts are provided with the same reference symbols or with the same component designations, whereby the disclosures contained in the entire specification can be analogously applied to the same parts having the same reference symbols or the same component designations. Also, position information selected in the specification, such as, for example, at the top, at the bottom, on the side, etc., refer to the figure being directly described and shown, and must be transferred appropriately to the new position if the position is changed. Furthermore, individual characteristics or combinations of characteristics from the different exemplary embodiments that are shown and described can represent independent inventive solutions or solutions according to the invention, in and of themselves.

All the information concerning value ranges in the present specification is to be understood to mean that these comprise any and all partial ranges of these; for example, the statement 1 to 10 should be understood to mean that all the partial ranges, starting from the lower limit 1 and the upper limit 10, are included, i.e. all partial ranges begin with a lower limit of 1 or greater and end at an upper limit of 10 or less, for example 1 to 1.7 or 3.2 to 8.1 or 5.5 to 10.

The exemplary embodiments show possible embodiment variants of the housing for the electronic device, whereby it should be noted at this point that the invention is not restricted to the specifically shown embodiment variants of the same, but rather diverse combinations of the individual embodiment variants with one another are possible, and this variation possibility lies within the ability of a person skilled in the art of this technical field, because of the teaching for technical action provided by the present invention. Therefore all conceivable embodiment variants that are possible by combining individual details of the embodiment variant that is shown and described are also covered by the scope of protection.

FIGS. 1 to 6 show a variant for the production of an electronic device having a housing 100 made of glass. In a first step, a hollow body 2 made of glass is produced or made available. In this case, it is assumed that a tube 2 made of glass is involved. In a further step, at least one electronic device 3 is introduced through an opening of the tube 2. As is evident from FIG. 1, multiple devices 3, spaced apart from one another, are introduced right away.

This exemplary electronic device 3 comprises a camera 4 (or, respectively, an image recording device such as an image recognition chip, for example), a microprocessor 5, as well as an antenna 6. In this example, it is assumed that the microprocessor 5 also comprises components for wireless communication. Together with the antenna 6, a wireless module and/or a transponder is formed in this manner. The camera 4, the microprocessor 5, and the antenna 6 are each disposed on a circuit board 7 having a conventional construction.

In FIG. 2, it is shown that the region between two electronic devices 3 is irradiated with a laser 9 in the melting region 8. In advantageous manner, differently great forces can be exerted on the tubular housing 2, for example a tube having a cylindrical or polygonal cross-section, during the severing and/or closing process of the tubular housing 2, on the inside and outside of the housing 2 in the region of the severing location 8, in the longitudinal direction of the housing 2. Thus, it is possible, for example, to apply a tensile stress (see arrows) to the parts of the tubular housing 2 to be severed, or to apply a differently great pressure force to the inside and outside of the housing 2 in the region of the severing location 8.

In FIG. 3, it is shown that the irradiation with the laser 9 in the melting region 8 and the accompanying heating or plastification of the glass, in combination with the tensile stress, leads to lengthening and constriction of the tube 2.

In FIG. 4, even greater constriction of the tube 2 is shown, and in FIG. 5, finally, severing of the tube 2 is shown. As is evident from FIG. 5, during this process, not only is the tube 2 severed, but at the same time, the resulting ends are also closed off by the softened/melted material, thereby causing face walls 10 and the housing 100 to be formed at the severing location 8.

This process is now repeated in every region between electronic devices 3, so that piece by piece, completely closed glass housings 100 enclosing a cavity 12 are formed around the electronic devices 3, as shown in FIG. 6. The housing 100 consists, in this case, of a cylindrical center part and two convex face walls 10 disposed on the face sides of the same, which walls essentially have the shape of a spherical dome or a spherical dome section. In particular, the face walls 10 can be formed by emission of energy with nanosecond or picosecond pulses and/or with continuous introduction of energy, for example by means of a gas flame. The housing 100 is produced in one piece from a single basic material, in this example from glass. However, it could also be produced from silicon, for example.

It is also conceivable, of course, that the housing 100 is built up from multiple components. For example, the center part 11 and the face walls 10 can be present as separate components. Further examples of multi-part housings are shown in FIGS. 10 to 13 and 17 to 23. For a good connection of the housing parts, it is advantageous if these are produced from a single basic material (e.g. glass or silicon) or at least have essentially the same physical and chemical properties.

In the preceding example, the hollow body 2 was only subject to tensile stress. It is also conceivable, however, that the hollow body 2 alternatively or additionally has an elevated air pressure applied to it, so that a higher air pressure prevails outside of the hollow body 2 than inside of it. In this manner, constriction of the hollow body 2 when heated in the melting region 8 can also be promoted.

It is furthermore conceivable that a relative rotation about the axis of the hollow body 2 is performed between the hollow body 2 and the laser 9. In other words, a laser 9 or multiple lasers 9 can be rotated around the hollow body 2, or the hollow body 2 itself is rotated relative to the laser 9/the lasers 9. In this manner, the melting region 8 can be heated uniformly.

The method for production of a housing 100 having at least one hermetically sealed accommodation space 12 for an electronic device 3, comprising at least a part of an interior of the housing 100, therefore comprises the steps:

producing/making available a hollow body 2 made of glass, having at least one opening, introducing, positioning and/or fixing in place at least one electronic device 3 through the at least one opening, hermetically sealing the accommodation space 12 by means of melting the housing 100, or closing off and welding the at least one opening by means of heat effect by means of laser radiation and/or a gas flame.

It is advantageous, in this connection, if the laser radiation is emitted in nanosecond and/or picosecond energy pulses and/or with continuous introduction of energy, because the power emitted can be well influenced in this way.

It is also advantageous if differently great forces are exerted on the inside and outside of the housing 100 in the region of the severing location 8, in the longitudinal direction of the housing 100, during the severing and/or closing process of the tubular housing 100. In particular, a differently great pressure force can be exerted on the inside and outside of the housing 100 in the region of the severing location 8, during the severing and/or closing process of the tubular housing 100. Thus, a face wall 10 of the housing 100 can be heated by heating the end region of the center part 11, by means of a laser, by emission of nanosecond and/or picosecond energy pulses and/or with continuous introduction of energy, and a face wall 10 can be formed by means of different great forces exerted on the inside and outside of the housing 100 in the region of the severing location 8, in the longitudinal direction of the housing 100. In particular, multiple electronic devices 3 can be introduced into, positioned and/or fixed in place in a tubular housing 100, at a distance from one another in the longitudinal direction, one after the other, through the at least one opening, whereupon the housing 100 is heated by means of laser radiation, by emission of nanosecond and/or picosecond energy pulses, in the intermediate region'8 between the electronic devices 3, and the tubular housing 100 is closed off with a face wall 10, by means of differently great forces exerted on the inside and outside of the housing 100 in the region of the severing location 8, in the longitudinal direction of the housing 100, on both sides of the intermediate region.

It is advantageous, because of the camera 4, if the dew point of the water vapor in the air in the housing, at least in its hermetically sealed partial space, amounts to 0°, preferably to between −10° C. and −30° C. In this way, the residual moisture in the housing 100 is so low that no condensation or no fogging on the inside of the housing 100 can come about.

FIGS. 7 and 8 now show a production method very similar to that of FIGS. 1 and 6, but the electronic devices 3 are now disposed on a common circuit board 7, which is severed by the laser 9 in the melting region 8. Thereby the circuit board 7 is severed and a housing 100 for the electronic device 3 is formed in one work step, as shown in FIG. 8. Here, too, the ends of the tube 2 are closed off by the softened/melted material, and face walls 10 are formed in the severing region 8. In this connection, the face walls 10 are essentially planar. In general, a face wall 10 can, of course, be configured to be not only convex but also concave.

In general, it should be noted that in practice, the severing process is started not as shown in FIGS. 1 to 8, in the center of the tube 2, but rather normally at an end of the same, so that a housing is always completed on one side of the laser 9. In practice, production of the housings 100 thereby takes place as shown in FIG. 6, whereby the tube 2 is pushed one position to the right, in each instance. In this connection, the first open end of the tube 2 (when starting the production process) is not necessarily closed off by means of severing of the tube 2, but rather can simply be melted/welded.

FIG. 9 shows an expansion of the electronic devices 3 to the effect that a tritium gas light source 13 is disposed in the region of the camera 4, and thermal barriers or insulations 14 are provided. The latter are supposed to protect sensitive devices such as the microprocessor 5, for example, from excessive heating by the laser 9. Of course, an insulation 14 can also be disposed in front of the camera 4, if it has an opening for the lens of the camera 4 or is transparent in this region.

To form the tritium gas light source 13, the tube 2 can be provided, in the region of the camera 4, as shown in FIG. 9, with a fluorescent and/or phosphorescent layer composed of a substance that can be excited to produce light by means of decay radiation, for example in ring shape, and the housing 100 of the electronic device 3 can be filled with a medium that emits decay radiation. For example, openings can be provided in the tube 2, for this purpose, which openings are closed off after the filling process (compare also FIG. 10 as well as FIGS. 17 to 23).

Alternatively, an LED or a luminescent material with afterglow properties can be provided as a light source.

It is advantageous if zinc sulfide (ZnS) is used as a fluorescent and/or phosphorescent substance, phosphoric acid ($H_3PO_4$) is used as an adhesive for the ZnS, and tritium gas is used as a medium that emits decay radiation. However, other combinations can of course fundamentally also be used for the production of a self-luminous region.

FIG. 10 shows a possibility for preventing excessive heating of the tube 2 outside of the melting region 8. For this purpose, a cooling cuff 15 can be provided. In this example, this cuff is disposed only to the left of the melting region 8, but of course it can also be disposed on both sides of the melting region 8.

In addition or alternatively to this, the tube 2 can also have a cooling medium flowing through it during the severing process. For this purpose, special flushing bores 16 are provided. Nitrogen ($N_2$), argon (Ar) or helium (He), for example, are possible flushing media. The flushing bores 16 can be welded shut when they are no longer needed. For example, this can be done using the laser 9, another laser, or in some other manner. For example, the flushing bores 16 can also be glued shut.

It is also advantageous if the emission of the energy of the laser pulses is controlled with a control apparatus, in such a manner that the temperature in the interior of the housing 100 is kept below a value of 200° in a region that is at a distance of equal to or greater than 2 mm from the location of action of the laser beams, because then the electronic device 3 is not damaged.

Another advantage of the method presented is that the water vapor content in the housing 100 that is produced is very low, because of the use of a dry flushing gas or filling gas such as $N_2$ or He. In this way, condensation of water vapor on the inside of the housing 100 at the operating temperature of the electronic device 3 can be advantageously prevented.

FIG. 11 now shows an exemplary and schematically shown electronic device 3 having a housing composed of two housing parts 101 and 102, made of glass, in detail. In this example, the two housing parts 101, 102 are connected using a weld seam 17, which can particularly be produced using a laser. It is advantageous if the weld seam 17 is disposed at a slight incline for this purpose.

Aside from the thermal insulation 14, the housing 101, 102 also comprises a partition wall 18 firmly connected with it, thereby forming a first hermetic cavity 19 and a second cavity 20. A microprocessor 5 and an energy source 21 of an electronic device 3 are situated in the first cavity 19. A sensor 22 is situated in the second cavity 20, which sensor is connected with the energy source 21 and with the microprocessor 5, respectively, by way of lines 23. In this connection, the lines 23 are guided through the partition wall 18 in such a manner that no substantial exchange of gases can take place between the cavity 19 and the cavity 20. The sensor 22 stands in more or less direct contact with the surroundings of the housing 101, 102 by way of passage holes 24. The holes 24 can be air-permeable and/or liquid-permeable. The sensor 22 can therefore be configured as a gas sensor, pressure sensor, pH sensor or the like, for example.

The conductors 23 can be used for power transmission and/or data transmission, for example. In general, the conductors 23 can be configured as wires. It is also conceivable, however, that a conductive paste or a conductive adhesive is introduced into the corresponding bores, which paste or adhesive, on the one hand, is provided for the electrical connection to the circuit board 7, and on the other hand is simultaneously provided also for the electrical connection through the partition wall 18. For example, a solder paste can be introduced and heated (melted). In addition or alternatively, the bore can also be metallically coated. In general, processes such as those known for circuit board production, for example, for the production of what are called "vias" or interlayer connections, can be used for the production of a conductive connection through the partition wall 18.

Fundamentally, bores for passing through desired media can be provided in the partition wall 18. For example, lines for liquid transport or gas transport can be provided. Of course, it is also conceivable that light guide fibers are passed through the bores.

The said techniques are, of course, also suitable, without restrictions, for passing any desired lines through the housing 101, 102.

Particularly if tritium gas light sources 13 are used, it is advantageous if the partial spaces 19, 20 are configured to be gas-tight, particularly tritium-gas-tight.

Because the electronic device 3 (particularly the microprocessor 5 and the energy source 21) is well protected against external chemical influences by the glass housing 101, 102, and the glass housing 101, 102 itself practically does not react with other chemical substances and itself does not emit any substances, the electronic device 3 is particularly well suited for use in organic tissue, for example in human and animal bodies as well as in plant tissue. It is also advantageous, in this connection, that the housing 101, 102 does not have any sharp edges. For example, the analysis and evaluation unit 22 can be configured for analysis and evaluation of bodily fluids and/or tissue samples. It is also possible to equip the electronic device 3 with means for movement from one location to another. Some exemplary principles in this regard are shown in FIGS. 14 and 15.

The energy source 21 can also be connected with an energy converter to which energy can be applied in contact-free manner, so that energy can be transmitted in contact-free manner and, above all, through the continuous housing wall 101, 102. For example, the energy converter can act inductively or, for example, can also convert movement energy of the capsule into electric energy, as is done in automatic watches, for example.

It is advantageous if at least one of the following components in the housing 101, 102, such as a light source 13, image recognition apparatus 4, image recording apparatus, electronic device, analysis, memory and evaluation unit 22 is connected with a transmitter 5, 6 for wireless transmission of data. In this way, the data can be transmitted to external processing units (e.g. remote PC).

It is also advantageous if at least one of the following components in the housing 100, such as a light source 13, image recognition apparatus 4, image recording apparatus, electronic device, analysis and evaluation unit 22 is connected with an energy source 21, because they can then be operated independent of an external energy supply.

FIGS. 12 and 13 now show two further possibilities for the production of a housing. In FIG. 12, for example, a conical face wall 103 is set onto a housing part 104 and welded/glued in place, and in FIG. 13, a housing is shown in which the housing parts 105 and 106 have an overlapping region at which they can be welded or glued, for example.

As has been mentioned, FIGS. 14 and 15 now show means for movement from one location to another for the electronic devices 3. In the left image of FIG. 14, a mass 25 is disposed within the housing 100, which mass can be deflected translationally, for example using an electromagnet. If the mass 25 is slowly moved to the left, for example, but, in contrast, quickly moved to the right, the capsule as a whole is moved to the left. The capsule can now be moved from one location to another by means of repeated deflection.

The right image of FIG. 14 shows a very similar principle, but with an eccentric mass 26 that is mounted so as to rotate. This, like the mass 25, can be moved back and forth but also always in one direction, particularly at a varying angular velocity. In this way, the capsule can once again be moved from one location to another. Because of the mass that is mounted so as to rotate, on the one hand linear movements in all directions, transverse to the axis of rotation (mass 26 is moved back and forth) are possible, as are rotations about this axis of rotation (mass 26 is rotated in one direction). If the mass 26 is mounted so as to rotate about two axes that stand transverse to one another, or if two masses 26 that are mounted so as to rotate about different axes are provided, then the capsule can be moved or rotated in any desired direction.

FIG. 15 furthermore shows drives according to the repulsion principle. In the left image, a container 27 that stands under pressure is provided, from which container the content is drained in controlled manner, using the valve 28, and the capsule can be moved from one location to another, accordingly, in this manner. Also, substances that bring about an increase in pressure in the container 27 can react chemically with one another in the interior of the container 27.

The right image shows a repulsion drive (jet drive) using a pump 29 for liquid media or, respectively, using a compressor for gaseous media, depending on the medium in which the capsule is used.

Of course, the principles shown in FIGS. 14 and 15 can also be combined in any desired manner. For example, the pump/the compressor 29 can be combined with a mass 26 mounted so as to rotate, so that the capsule can be moved in any desired direction. Of course, steering jets or steering openings that face radially outward can also be used for rotating the capsule.

The left image in FIG. 16 now shows an electronic device 3 in a housing 100 in which micro-bores 30 are disposed, which are gas-permeable but liquid-impermeable. The electronic device 3 can be cooled using these micro-bores 30. Furthermore, in this manner the formation of an undesirable differential pressure between the interior of the housing 100 and its surroundings can be prevented, for example if the medium situated in the interior of the housing is heated or cooled. In this way, explosion or implosion of the housing 100 can be effectively prevented, something that would have unintended consequences particularly in the case of use in the human or animal body.

However, it can be undesirable for the electronic device 3 to be exposed to gases that penetrate through the micro-bores 30. For this reason, it is provided, in a preferred variant, that the housing 100 with the electronic device 3 is introduced into a further hermetic glass housing 31 in which micro-bores 30 are disposed, which are gas-permeable but liquid-impermeable. In this case, the inner housing 2 does not need to have any micro-bores. In this way, the electronic device 3 can be cooled with being exposed to the gases that pass through the micro-bores 30. If the housing 100 is nevertheless destroyed by means of implosion or explosion, the destroyed housing 100 is held in the interior of the housing 31 and cannot cause any further damage.

In general, it is advantageous if a wall thickness of the housing 100 and/or 31 amounts to between 0.05 to 5 mm, at least in the center region between two face walls, in order to guarantee sufficient mechanical stability.

FIG. 17 now shows an intermediate stage in the production of a housing for an electronic device according to another method. In concrete terms, FIG. 17 shows an exemplary first housing part 107 and an exemplary second housing part 108 made of glass, for the said housing, as well as an electronic device 3 in an exploded representation. The method for the production of the housing 107, 108 will now be explained in greater detail using FIG. 17.

The method comprises the steps:
  making at least one depression 32 in at least one housing part 107 of a housing,
  producing at least one cavity by means of joining the housing parts 107, 108 together, wherein at least one opening 33, particularly at least two openings 33, remains/remain open into the cavity from the outside,
  introducing an electronic device 3 into the at least one cavity through the at least one opening 33, and
  closing off and welding the at least one opening 33 by means of laser radiation.

In particular, the two housing parts 107, 108 can be welded to one another by means of laser radiation with energy emission in the nanosecond and/or picosecond range and/or with continuous introduction of energy.

For example, the depression 32 can be milled into the housing part 107. It is also conceivable, however, that the depression is produced using an ion bean, a material removal method, for example with a laser or powder blasting. Likewise, the grooves provided for the feeder openings 33 can also be milled, for example, or produced by means of an ion beam. A cavity having two feeder openings 33 is then formed by means of setting the second housing part 108 onto the first housing part 107. For example, the housing part 108 can be glued onto the housing part 107 or welded to it, particularly using a laser.

A fluorescent and/or phosphorescent layer can be produced on at least one delimitation wall of the cavity. The method then comprises the steps:
  making at least one depression 32 in the first housing part 107, producing at least one cavity by means of covering the at least one depression 32 with the at least diffuse second housing part 108, wherein two feeder openings 33 remain open into the cavity from the outside, producing a fluorescent and/or phosphorescent layer formed from a substance that can be excited to produce light, by means of decay radiation, on at least part of a delimitation wall of the at least one cavity, introducing a medium that emits a decay radiation for a substance that can be excited to produce light into the at least one cavity, through the at least one feeder opening, and melting/welding the at least one opening after introduction of the electronic device 3.

For a method for the production of self-luminous bodies, the method can also comprise the following steps:

making at least one depression 32 in at least one housing part 107 of a housing, producing a fluorescent and/or phosphorescent layer 36 formed from a substance that can be excited to produce light, by means of decay radiation, and/or a mask 41 on at least part of a delimitation wall 37 of at least one cavity 34, producing the at least one cavity 34 by means of joining the housing parts 107, 108 together, welding the housing parts 107, 108 by means of laser radiation, by emission of nanosecond and/or picosecond energy pulses and/or with continuous introduction of energy, wherein at least one feeder opening 33, particularly at least two feeder openings 33, remains/remain open into the cavity 34 from the outside, introducing a medium 38 that emits a decay radiation for a substance 36 that can be excited to produce light, or the substance 36 and the medium 38, into the at least one cavity 34, through the at least one feeder opening 33, and closing off and welding the at least one feeder opening 33 by means of laser radiation.

For example; the fluorescent and/or phosphorescent layer can be produced in that the at least one housing part 107, 108 is coated with adhesive (e.g. phosphoric acid $H_3PO_4$), and subsequently a fluorescent and/or phosphorescent substance (e.g. zinc sulfide ZnS) is applied to the adhesive layer.

It is conceivable that the adhesive and subsequently the fluorescent and/or phosphorescent substance that forms the fluorescent and/or phosphorescent layer is/are introduced into the cavity through one of the two feeder openings 33. For this purpose, one of the two feeder openings 33 can be connected with an inflow line, and the other feeder opening 33 can be connected with an outflow line. Adhesive can be introduced into the cavity by way of the inflow line, in the form of a liquid or in the form of a mist, and excess adhesive can be conducted away by way of the outflow line. In the same manner, the fluorescent and/or phosphorescent substance can be introduced into the cavity or conducted away from it, either by way of the same lines or by way of separate lines.

In a further variant of the method, the adhesive layer is applied to the housing part 107 and/or the housing part 108 before the two parts are joined together. In a further step, the housing part 107 and the housing part 108 are joined together, and subsequently the fluorescent and/or phosphorescent substance is introduced by way of the feeder openings 33. This variant has the advantage that the adhesive can be applied very selectively to at least one of the housing parts 107, 108, for example sprayed on or rolled on, specifically using a mask. It is also conceivable that the adhesive is imprinted or stamped on, and in this way selective wetting of the housing part 107 and/or of the housing part 108 with adhesive can be produced. The selective adhesive application can take place, for example, in the form of letters, numbers, symbols or other geometric shapes or any desired surfaces. When the fluorescent and/or phosphorescent substance is subsequently introduced into the cavity, it deposits on the wetted surfaces and also forms letters, numbers, symbols, etc. Furthermore, it is conceivable that not only is the adhesive applied to the housing part 107 and/or the housing part 108, but also the fluorescent and/or phosphorescent substance is applied to the adhesive layer before the housing parts 107, 108 are joined together. Finally, it is also possible that the fluorescent and/or phosphorescent substance itself has adhesive or adhering properties. Separate adhesive application can then be eliminated. For example, a mixture of phosphoric acid ($H_3PO_4$) and zinc sulfide (ZnS) can be applied directly.

A self-luminous medium or a medium that can be excited to produce light (e.g. tritium gas) is then introduced into the finished cavity, provided with the fluorescent and/or phosphorescent layer, wherein once-again, the two feeder openings 33 can function as inflow and outflow.

In a further step, the feeder openings 33 are closed off, for example glued shut or welded shut.

FIG. 18 now shows a top view of and a cross-section through an exemplary housing for the electronic device 3. In this connection, once again a housing part 109 and a housing part 110 are connected with one another, thereby causing a cavity 34 to be formed from a depression 32 and feeder openings 33 to be formed from grooves in the housing part 109. In this example, it is assumed that the top side of the cavity 34 is equipped, over its full area, with an adhesive layer 35 and, on top of that, with a fluorescent and/or phosphorescent layer 36. Thereby the surface 37 of the cavity 34 is partly equipped with the fluorescent and/or phosphorescent layer 36. The layer 36 begins to produce light by means of the medium 38 situated in the cavity 34, which medium emits decay radiation.

On the outer surface 39 of the housing part 110 itself, facing away from the cavity 34 (in other words on the side opposite to the base surface 40), a light-impermeable or at least light-weakening mask 41 is still disposed. In this layer, holes in the shape of the numbers 3, 6, 9, and 12 are provided. As can easily be imagined, the light produced in the cavity 34 or in the fluorescent and/or phosphorescent layer 36 penetrates through these holes, thereby making it possible to produce a self-luminous face of a watch. In this connection, the numbers appear bright on a dark background.

Of course, it would also be possible to eliminate the mask 41 and to form the numbers directly using the fluorescent and/or phosphorescent substance 36, instead, for which purpose one of the methods mentioned above can be used. The numbers then also appear bright on a dark background. It would also be conceivable to produce a negative image of the numbers. The numbers then appear dark on a bright background. In particular, if no mask 41 is used, the arrangement presented can also be used directly as a watch crystal or as a watch body, in general. For example, the hands can move in the cavity 34 of this arrangement. However, the housing part 110 could also be configured as an LCD display, thereby making it possible to implement a backlighted display. Of course, the mask 41 can also be disposed between the housing part 109 and the housing part 110. In this application case, the electronic device 3 itself can comprise a circuit for determining the time of day and, for example, also the motors for driving watch hands (not shown).

In general, the housing part 109 and the housing part 110, as well as, if applicable, the mask 41 can be connected with one another by means of fusion bonding (bonding of the boundary surfaces by means of van der Waals' forces) or also by means of anodic bonding (chemical bonding at the boundary layers, which is initiated by means of electrical attraction forces). The housing parts 109 and 110 as well as the mask 41 can also, however, be welded together using a laser. The feeder openings 33 can be welded, as shown in FIG. 18, using a laser (e.g. $CO_2$ laser, fiber laser, etc.), or can also be glued or provided with a plug.

In FIGS. 17 and 18, housings 107 ... 110 having only one cavity 34 were shown. Of course, a housing 107 ... 110 can also comprise more than one cavity 34. These can be connected in chain-like manner with connection lines, for example, and/or can be provided with feeder openings 33 that lead to the outside, in each instance.

Furthermore, it is possible that a cavity 34 has only one feeder opening 33 or also three or more feeder openings 33. In particular, if only one feeder opening 33 leads to a cavity 34, concentric lines, for example, can serve for inflow and outflow of the substance to be conveyed into/out of the cavity.

FIG. 19 shows a further variant of a housing 111 ... 112 for an electronic device 3, which is very similar to the variant shown in FIG. 17. In place of a groove, however, here bores are provided as feeder openings 33 (for example with a diameter in the range of 3 μm to 2 mm). These bores can be produced mechanically, for example, using a drill, a laser beam or an ion beam.

FIG. 20 shows a further variant of a housing for an electronic device 3, in which holes are disposed in the housing part 113 as feeder openings 33, as in FIG. 19. In contrast to the variant from FIG. 16, however, the housing part 114 is somewhat smaller here than the housing part 113, and is inserted into a depression of the same. In this case, the housing part 113 and the housing part 114 are welded to one another using a weld seam 42. Furthermore, the feeder opening 114 is not welded as in FIG. 16, but rather closed off with a plug 43. In this example, the self-luminous body is structured not as a watch face or watch crystal, but rather as a lighting body. In this case, the electronic device 3 can be structured as a transponder that can be read out in contact-free manner (RFID tag), for example, which contains an identification of the lighting body.

FIG. 21 now shows a housing 115, 116 that is very similar to the housing 113, 114 shown in FIG. 20. In contrast to this, however, a frame-shaped mask 41 is set onto the housing part 116, which mask prevents light from shining through in the edge region of the self-luminous body.

In FIG. 21, the fluorescent and/or phosphorescent layer 36 is disposed on the top side of the cavity 34, as an example, specifically directly on the housing part 116. This layer is structured in such a manner that a face of a watch is obtained. No separate adhesive layer is provided, for example because a mixture of phosphoric acid ($H_3PO_4$) and zinc sulfide (ZnS) and/or zinc oxide (ZnO) was applied directly.

Furthermore, supports 44 are provided in the cavity 34 in FIG. 21, so that the housing parts 115, 116 cannot bend excessively. For example, the supports 44 can be formed onto the housing part 115 or housing part 116 directly, and glued to the other housing part 115, 116, in each instance, for example. Of course, it is also conceivable that the supports 44 merely touch the other housing part 115, 116, in each instance, in other words are not permanently connected with it. As a further possibility, the supports 44 can also be present as separate components, which are connected with a housing part 115, 116 or with both housing parts 115, 116. Finally, the supports 44 can also touch the electronic device 3 or be connected with it, as shown in FIG. 21.

In general, the self-luminous bodies shown in FIGS. 17 to 21 can be configured as blocks and therefore can have a rectangular or square base surface 40. Of course, other shapes are also conceivable. In particular, the base surface 40 can be configured elliptically or in circular shape (see, in this regard, the alternative outline, shown with a broken line, in the top view of FIG. 21). Specifically, the self-luminous body can have a housing 107 ... 116 configured as a block or flat piece, which is formed by two essentially plate-shaped housing parts 107 ... 116 having a polygonal or elliptical or circular base surface 40, wherein the sum of the heights h of the two housing parts 107 ... 116 that are perpendicular to the base surface is less than a shorter side length s or a minimal diameter d or radius of the same.

In general, the electronic device 3 of FIGS. 17 to 21 can comprise a camera 4. In this case, the fluorescent and/or phosphorescent layer 36 can serve to illumine the viewing field of the camera 4, and is then not necessarily structured in the form of letters and the like.

Vice versa, the teaching with regard to the application of a fluorescent and/or phosphorescent layer disclosed with reference to FIGS. 17 to 21 can also be applied to the embodiments of FIGS. 1 to 17.

FIG. 22 now shows a further embodiment that combines the characteristics of FIG. 12 or FIG. 16, respectively, and FIGS. 17 to 21. In concrete terms, passage holes 24 or micro-bores 30 are disposed in the housing parts 117, 118. Furthermore, electrical conductors 23 are disposed in the housing part 117, which serve for contacting of the electronic device 3.

FIG. 23 shows an alternative form of housing parts 119, 120, which are configured essentially in U shape. A hollow body that is open on one side is formed by connecting the housing parts 119, 120, which body can be closed off by a face wall, not shown, for example.

FIG. 24 shows a further exemplary housing, shown schematically, having an electronic device 3 disposed in it. The housing part 121, which is formed similar to a test tube, is connected with a plate-shaped housing part 121 using a weld seam 17. The two housing parts 121 and 122 consist of glass, in this example, and can particularly be welded using a laser. The electronic device 3 shown schematically comprises a microprocessor 5, in this example, which is soldered onto a circuit board 7. Furthermore, electrical conductors 23 are connected with the circuit board 7, which conductors are passed through passage holes 24, and can serve for supplying electric power, as control lines or for picking up sensor signals.

FIG. 25, finally, shows an arrangement that is very similar to the arrangement shown in FIG. 24. In contrast to it, however, the housing comprises a tubular housing part 123, which is connected with, particularly, once again, welded to plate-shaped housing parts 124 and 125.

The variants of the housing 100 ... 125 for an electronic device 3 shown in the figures show independent embodiments, in and of themselves, if applicable, where the same reference symbols or component designations are used for the same parts.

The special embodiment details shown with regard to the different variants do not necessarily relate only to the figure in question, but can also be used in other embodiments, if applicable. For example, the insulation layers of FIG. 9 can be used analogously also in a variant according to FIGS. 17 to 23. Likewise, it is conceivable that the variants according to FIGS. 17 to 23 are cooled as in FIG. 10.

Furthermore, it should be pointed out that use of the arrangements presented is, of course, not restricted to watch construction. For example, use as an informational sign, emergency lighting, door sign, keyboard background lighting and the like is also conceivable.

As has been mentioned, the electronic devices 3 enclosed by the glass housing 100 . . . 125 can particularly be used also in the human or animal body as well as in plants. In this connection, it is possible for the devices 3 to be surgically implanted. For this purpose, the outer surface of the housing 100 . . . 125 can be roughened and/or provided with substances/structures that promote growth of human/animal/plant tissue on it. It is also possible, however, to apply other coatings, coats or layers such as silicones, antistatic, bacteria-inhibiting, dirt-repelling and/or adhesive materials.

The housing 100 . . . 125 or a hermetically sealed partial space 19, 20 of the same is diffusion-tight, i.e. the water vapor permeability ($s_d$) is preferably greater than 2,500 m based on the determinations in DIN 4108-3.

The rounded capsules shown in FIGS. 1 to 16, in particular, can also be provided to be swallowed. It is advantageous if the outer surface of the housing is coated with a gel and/or a flavor carrier, in order to facilitate swallowing.

Of course, however, an embodiment according to FIGS. 17 to 23 can also be intended for swallowing, and an embodiment according to FIGS. 1 to 16 can be intended for implantation. It is advantageous, in this connection, if the surface of the housing is treated for the purpose, in each instance.

In general, housing parts 101 . . . 125 can be configured to be completely transparent, diffuse or opaque (of course, intermediate stages are possible, in this connection). For example, the diffuse or opaque parts of the housing 100 . . . 125 or of the cover layer can be disposed adjacent to the melting or welding regions 8, thereby particularly making it possible to connect housing parts 101 . . . 125 having different optical properties with one another. Another possibility is also to provide the housing 100 . . . 125 or at least a part of the housing 100 . . . 125 or of the cover layer with a functional coating, for example a film, which has different optical properties. For example, the functional coating, for example the film, can be configured to be diffuse or opaque. Of course, it is also conceivable to influence other physical properties, such as the electrical conductivity, for example, using a functional coating.

For the sake of good order, it should be pointed out, in conclusion, that for a better understanding of the structure of the arrangements presented, these and their components were shown not to scale and/or enlarged and/or reduced in size, in part.

The task on which the independent inventive solutions are based can be derived from the specification.

Above all, the individual embodiments shown in FIGS. 1 to 23 can form the object of independent solutions according to the invention. The tasks and solutions according to the invention, in this regard, can be derived from the detailed description of these figures.

REFERENCE SYMBOL LIST

100 . . . 125 housing, housing parts
2 tubular base body
3 electronic device
4 camera
5 microprocessor
6 antenna
7 circuit board
8 melting region/welding region/severing region
9 laser
10 face wall
11 (tubular) center part
12 cavity
13 tritium gas light source
14 thermal barrier/insulation
15 cooling cuff
16 flushing bore
17 weld seam
18 partition wall
19 first cavity
20 second cavity
21 energy source
22 readings recorder
23 electrical conductor
24 passage holes
25 linearly movable mass
26 eccentrically mounted rotatable mass
27 pressurized container
28 valve
29 pump/compressor
30 micro-bore
31 outer housing
32 depression
33 feeder opening
34 cavity
35 adhesive layer
36 fluorescent and/or phosphorescent layer/substance
37 surface of the cavity
38 medium emitting decay radiation
39 top surface of the housing
40 base surface of the housing
41 mask
42 weld seam
43 plug
44 supports
d diameter
g height
s side length

The invention claimed is:

1. Method for the production of a housing having at least one hermetically sealed accommodation space for an electronic device, said accommodation space comprising at least a part of an interior of the housing, comprising the steps:
   producing/making available a hollow body made of glass or silicon, having at least one opening,
   introducing, positioning and/or fixing in place at least one electronic device through the at least one opening, and
   closing off and welding the at least one opening by means of laser radiation, and
   wherein the laser radiation is formed by means of nanosecond and/or picosecond pulses.

2. Method according to claim 1, wherein a heat insulator or a heat protection layer is disposed between the device and a melting region or a welding region.

3. Method according to claim 1, wherein a partition wall is inserted into the interior and welded to the housing to form first and second accommodation spaces, and the first and second accommodation spaces are hermetically separated from one another to form first and second hermetic accommodation spaces.

4. Method according to claim 3, wherein openings are disposed in the partition wall between the first hermetic accommodation space and the second hermetic accommodation space, which openings can be hermetically sealed by means of light guides, electric lines or conductive contact masses.

5. Method according to claim 3, wherein micro-bores that are gas-permeable and liquid-impermeable are disposed in the second accommodation space of the housing, which second accommodation space is separated from the first hermetic accommodation space of the housing.

6. Method according to claim 1, wherein an electronic device and/or an energy source is/are disposed in a first hermetically sealed accommodation space.

7. Method according to claim 6, wherein at least one of the elements selected from the group consisting of an electronic device, an analysis apparatus, and a readings recorder is disposed in an accommodation space adjacent to the first hermetically sealed accommodation space.

8. Method according to claim 1, wherein a camera is introduced into the cavity.

9. Method according to claim 1, wherein a wireless module and/or a transponder is/are introduced into the cavity.

10. Method according to claim 1, wherein a mass moved by a motor is introduced into the cavity.

11. Method according to claim 1, wherein a repulsion drive having a passage opening in the housing is introduced into the cavity.

12. Method according to claim 1, wherein a tritium gas light source is disposed in the cavity.

13. Method according to claim 1, wherein multiple electronic devices are introduced, positioned and/or fixed in place in a tubular housing, at a distance from one another in a longitudinal direction, one after the other, through the at least one opening, whereupon the housing is heated by means of pulsed laser radiation formed by nanosecond and/or picosecond energy pulses in an intermediate region between the electronic devices, and the tubular housing is closed off with a face wall, by means of differently great forces exerted on the inside and outside of the housing in a region of the severing location, in the longitudinal direction of the housing, on both sides of the intermediate region.

14. Method according to claim 13, wherein a face wall of the housing is heated by heating an end region of a center part by means of a laser, by emission of nanosecond and/or picosecond energy pulses, and differently great forces exerted on the inside and outside of the housing in the region of the severing location form a face wall, in the longitudinal direction of the housing.

15. Method according to claim 13, wherein the inside and outside of the housing have a differently great pressure force exerted on them in the region of the severing location, during a severing process and/or a closing process of the tubular housing.

16. Method according to claim 1, wherein at least one end of a tubular base body is melted/welded for the production of the housing.

17. Method according to claim 1, wherein a tubular base body is severed by means of melting it, for production of the housing, wherein the melted material closes off the resulting ends.

18. Method according to claim 17, wherein differently great forces are exerted on the inside and outside of the housing in the region of the severing location, in the longitudinal direction of the housing, during the severing process and/or closing process of the tubular housing.

19. Method according to claim 1, wherein the housing is configured as a block.

20. Method according to claim 1, wherein the housing is formed by essentially plate-shaped first and second housing parts having a square or rectangular base surface, and the sum of the height of the first and second housing parts that are perpendicular to the base surface is less than a shorter side length of the same.

21. Method according to claim 20, wherein the first housing part is formed by a plate-shaped cover layer.

22. Method according to claim 21, wherein at least a part of the housing or of the cover layer is produced to be diffuse.

23. Method according to claim 1, comprising:
making at least one depression in at least one housing part of a housing,
producing at least one cavity by means of joining the housing parts together, wherein at least one opening remains open into the cavity from the outside,
introducing an electronic device into the at least one cavity through the at least one opening, and
closing off and welding the at least one opening by means of laser radiation.

24. Method according to claim 1, wherein the housing with the electronic device is introduced into a further hermetic glass housing, in which micro-bores that are gas-permeable and liquid-impermeable are disposed.

25. Method according to claim 1, wherein bores for passing through metallic wires and/or light-guide fibers are disposed in the housing.

26. Method according to claim 1, wherein the outer surface of the housing is coated with a gel and/or a flavor carrier.

27. Method according to claim 1, wherein the outer surface of the housing is roughened and/or provided with reactive substances/structures that promote growth of human/animal/plant tissue on it.

28. Method according to claim 1, wherein the emission of energy of the laser pulses is controlled with a control apparatus, in such a manner that the temperature in the interior of the housing is kept below a value of 200° C. in a region that is at a distance of equal to or greater than 2 mm from a weld seam or from the location of action of laser beams.

29. Method according to claim 28, wherein during application of heat energy by means of the laser radiation, the regions adjacent to the weld seam are cooled.

30. Method according to claim 1, wherein the laser radiation is formed additionally with the continuous introduction of energy.

31. Apparatus having a housing that is hermetically sealed, at least in part, composed of silicon, obtainable by a method according to claim 1, wherein the housing is produced in one piece from a single basic material or wherein the housing comprises multiple housing parts and is at least produced from a single basic material.

32. Apparatus according to claim 31, wherein the at least one hermetically sealed accommodation space is configured to be water-vapor-tight with a water vapor permeability $s_d$ greater than 2,500 m.

33. Apparatus according to claim 32, wherein the housing contains air having water vapor with a dew point, at least in the at least one hermetically sealed space, amounting to 0° C.

34. Apparatus according to claim 31, further comprising an analysis and evaluation unit configured for analysis and evaluation of bodily fluids and/or tissue samples.

35. Apparatus according to 31, wherein a wall thickness of the housing, at least in the center region, amounts to between 0.05 mm to 5 mm.

36. Apparatus according to claim 31, wherein the housing or a cover layer has diffuse or opaque parts disposed adjacent to melting regions or welding regions.

37. Apparatus according to claim 36, wherein at least a part of the housing or of the cover layer is provided with a functional coating.

38. Apparatus according to claim 37, wherein the functional coating is configured to be diffuse or opaque.

39. Apparatus according to claim 31, wherein the housing has first and second parts spaced apart from one another with support elements that are distributed over a cavity and oriented perpendicular to e base surfaces of the cavity.

* * * * *

UNITED STATES PATENT AND TRADEMARK OFFICE
CERTIFICATE OF CORRECTION

| | |
|---|---|
| PATENT NO. | : 9,572,273 B2 |
| APPLICATION NO. | : 14/424511 |
| DATED | : February 14, 2017 |
| INVENTOR(S) | : Blunier et al. |

It is certified that error appears in the above-identified patent and that said Letters Patent is hereby corrected as shown below:

In the Claims

Column 25, Line 15, (Claim 39) after the word "to" please delete: "e".

Signed and Sealed this
Twenty-eighth Day of March, 2017

Michelle K. Lee
*Director of the United States Patent and Trademark Office*